(12) United States Patent
Wakasugi et al.

(10) Patent No.: US 7,211,704 B2
(45) Date of Patent: May 1, 2007

(54) METHOD FOR PRODUCING P-DICHLOROBENZENE

(75) Inventors: Takashi Wakasugi, Fukushima (JP); Tsugio Nonaka, Fukushima (JP); Tadashi Miyakawa, Fukushima (JP); Takanobu Hanabusa, Fukushima (JP); Kazuhiko Sunagawa, Fukushima (JP); Shigeru Mizusawa, Fukushima (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 10/526,557

(22) PCT Filed: Sep. 3, 2003

(86) PCT No.: PCT/JP03/11223

§ 371 (c)(1),
(2), (4) Date: Oct. 12, 2005

(87) PCT Pub. No.: WO2004/022512

PCT Pub. Date: Mar. 18, 2004

(65) Prior Publication Data

US 2006/0106264 A1     May 18, 2006

(30) Foreign Application Priority Data

Sep. 4, 2002 (JP) .............................. 2002-258356

(51) Int. Cl.
*C07C 17/00* (2006.01)

(52) U.S. Cl. ..................................................... 570/210
(58) Field of Classification Search ................ 570/207, 570/208, 210
See application file for complete search history.

(56) References Cited

FOREIGN PATENT DOCUMENTS

| EP | 126669 A1 | 11/1984 |
|---|---|---|
| EP | 474074 A1 | 3/1992 |
| JP | 60-125251 | 7/1985 |
| WO | WO 97/43041 A1 | 11/1997 |

OTHER PUBLICATIONS

Cram et al.; *Organic Chemistry* 2nd Edition; c. 1964 & 1959; pp. 218 and 427.

*Primary Examiner*—J. Parsa
(74) *Attorney, Agent, or Firm*—McDermott Will & Emery LLP

(57) ABSTRACT

In a process for preparing p-dichlorobenzene by nuclear chlorination of benzene and/or chlorobenzene as the starting material with chlorine molecules, chlorination is carried out using aluminum chloride in an amount of 0.1–3 millimols per mol of the starting material and phenothiazines such as 10H-phenothiazine-10-carboxylic acid phenyl ester in an amount of 0.1–0.9 mols per mol of aluminum chloride so as to be a chlorination degree in a range of 1.2–2.5, by which p-dichlorobenzene can be obtained in a high para-selectivity and a short reaction time.

1 Claim, No Drawings

METHOD FOR PRODUCING P-DICHLOROBENZENE

TECHNICAL FIELD

The present invention relates to a process for preparing p-dichlorobenzene, which is an important starting material for high molecules, in a high para-selectivity and a short reaction time by ring-chlorination of benzene and/or chlorobenzene.

BACKGROUND ARTS

A nuclear chlorination reaction of chlorobenzene which is a step for producing p-dichlorobenzene is classified in an electrophilic substitution reaction exhibiting ortho-para orientation, which is known to be chlorinated by a chlorine molecule using a Lewis acid as a catalyst.

Cram & Hammond: "Organic Chemistry" 2nd edition, page 218 (1964) discloses aluminum chloride and ferric chloride as important Lewis acid. Moreover, in page 427, it is disclosed that one halogen atom of a halogen molecule combines with ferric halide or aluminum halide and the other halogen atom becomes cationic halogen to enhance electrophilic property.

Regarding 10-substituted-10H-phenothiazine which is used as a promoter together with the Lewis acid, there are following proposals in order to enhance the para-selectivity upon preparing p-chlorobenzene by nuclear chlorination of benzene and/or chlorobenzene using chlorine molecules and Lewis acid.

EP126669 (corresponding with Japanese Patent Application Laid-open SHO 59-206051) discloses 10-arylcarbonyl-10H-phenothiazine, 10-halocarbonyl-10H-phenothiazine and 10-$CH_xX^1_y$CO-10H-phenothiazine (wherein $X^1$ represents a chlorine atom or bromine atom, x is 0–2 and y is 1–3). EP474074 (corresponding with Japanese Patent Application Laid-open HEI 4-305544) discloses 10-$CF_3(CF_2)_n$CO-10H-phenothiazine (n=0, 1 or 2). WO97/43041 discloses 10H-phenothiazine-10-carboxylic acid phenyl esters.

EP126669 does not disclose aluminum compounds as the Lewis acid, but ferric chloride and antimony trichloride are used in Examples. It does not suggest that the aluminum chloride shows an effect superior to ferric chloride and antimony trichloride. EP474074 and WO97/43041 disclose aluminum chloride as the Lewis acid, but only ferric chloride is used in Examples. These references do not suggest that the aluminum chloride exhibits an effect superior to ferric chloride.

Although all the process disclosed in these three patent documents relates to the same proposals for improving the para-selectivity, there are still problems to be improved with respect to reaction time.

Japanese Patent Application Laid-open SHO 60-125251 discloses in Example 3 chlorination of toluene using a Lewis acid together with 10-trifluoroacetyl-phenothiazine as a catalyst system for improving the para-selectivity in nuclear chlorination of alkylbenzene. Table 1 in said reference however shows the fact that aluminum chloride has the para-selectivity inferor to that of ferric chloride and antimony trichloride.

DISCLOSURE OF THE INVENTION

As a result of various studies of finding out the catalyst system which enables nuclear chlorination in an excellent para-selectivity and a short reaction time, the present inventors have completed the present invention.

The present invention has the following constitutional feature.

The process for preparing p-dichlorobenzene according to the present invention comprises carrying out nuclear chlorination of benzene and/or chlorobenzene as a starting material with chlorine molecules, which is characterized by chlorinating using 0.1–3 millimoles of aluminum chloride per mol of the above-mentioned starting material and 0.1–0.9 moles of a phenothiazine compound of the following formula (I) per mol of aluminum chloride so that a chlorination degree is in a range of 1.2–2.5.

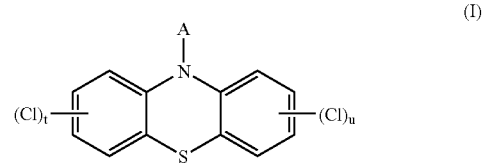

(I)

wherein t is an integer of 0–4 (preferably 0–3) and u is an integer of 0–4 (preferably 0–3). A is a halocarbonyl group and preferably chlorocarbonyl group; a group represented by $CH_xX^1_y$CO—, wherein $X^1$ is a chlorine atom or a bromine atom, x is an integer of 0–2, and y is an integer of 1–3, and preferably a dichloroacetyl group; a group represented by $CF_3(CF_2)_n$CO—, wherein n is an integer of 0–2, and preferably a trifluoroacetyl group; or a group represented by the following formula (II).

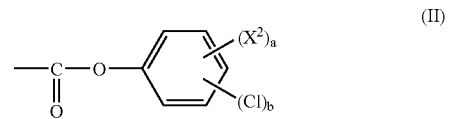

(II)

wherein $X^2$ is a halogen atom (preferably a fluorine atom or chlorine atom); an alkyl group having 1–4 carbon atoms (preferably a methyl group); an alkoxy group having 1–4 carbon atoms (preferably a methoxy group); a nitro group or a cyano group; a is an integer of 0–5 (preferably 0 or 1); a plurality of $X^2$ is identical or different respectively when a is 2 or more; and b is an integer of 0–5 (preferably 0–2), but (a+b) is an integer of 5 or less.

Comparison of the Present Invention with the Above-mentioned Prior Arts

In the following, the present invention will be illustrated in detail comparing with the prior arts.

EP126669 discloses in Examples 3, 10 and 13, production of p-dichlorobenzene from benzene by reacting 3 mols of benzene with 4.5 mols of chlorine at 60° C. for 4.5 hours using a catalyst system consisting of 10-substituted-10H-phenothiazine/ferric chloride in a molar ratio of 1.07–1.50 in an amount of 0.12–0.38 millimols of ferric chloride per mol of benzene, by which nuclear chlorination can be carried out in a para-selectivity of 82.1–83.4%.

The term "para-selectivity" herein means a value calculated by the formula {p/(o+p)×100} using value of gas chromatography of o-dichlorobenzene (value: o) and p-dichlorobenzene (value:p) in a reaction mixture after nuclear chlorination. It is hereinafter referred to as the same meaning.

EP126669 discloses in Example 4 production of p-dichlorobenzene from benzene by reacting 3 mols of benzene with 4.5 mols of chlorine at 60° C. for 4.5 hours using a catalyst system consisting of 10-substituted 10H-phenothiazine/antimony trichloride in a molar ratio of 1.53 in an amount of 0.066 millimols of antimony trichloride per mol of benzene, by which nuclear chlorination can be carried out in the para-selectivity of 82.8%.

EP126669 discloses in Example 5 production of p-dichlorobenzene from chlorobenzene by reacting 6 mols of chlorobenzene with 5 mols of chlorine at 20° C. for 5 hours using a catalyst system consisting of 10-substituted-10H-phenothiazine/ferric chloride in a molar ratio of 1.61 in an amount of 1.52 millimols of ferric chloride per mol of benzene, by which nuclear chlorination can be carried out in the para-selectivity of 87.3%.

EP474074 discloses in Examples 1, 2, 4 and 5 production of p-dichlorobenzene from benzene by reacting 1.28 mols of benzene with 140% by mol of chlorine at 60° C. for 5 hours using a catalyst system consisting of 10-substituted-10H-phenothiazine/ferric chloride in a molar ratio of 1.0 in an amount of 0.24 millimols of ferric chloride per mol of benzene, by which nuclear chlorination can be carried out in the para-selectivity of 81.3–83.0%.

EP474074 discloses in Example 3 production of p-dichlorobenzene from benzene by reacting 1.28 mols of benzene with 140% by mol of chlorine at 20° C. for 5 hours using a catalyst system consisting of 10-substituted-10H-phenothiazine/ferric chloride in a molar ratio of 1.0 in an amount of 2.46 millimols of ferric chloride per mol of benzene, by which nuclear chlorination can be carried out in the para-selectivity of 86.1%.

EP474074 discloses in Example 6 production of p-dichlorobenzene from benzene by reacting 0.89 mols of benzene with 60% by mol of chlorine at 70° C. for 2.5 hours using a catalyst system consisting of 10-substituted-10H-phenothiazine/ferric chloride in a molar ratio of 1.0 in an amount of 0.42 millimols of ferric chloride per mol of benzene, by which nuclear chlorination can be carried out in the para-selectivity of 82.0%.

WO97/43041 discloses in Preparation Example 2 production of p-dichlorobenzene from benzene by reacting 1.92 mols of benzene with chlorine at 60° C. for 5.5 hours using a catalyst system consisting of 10-substituted 10H-phenothiazine/ferric chloride in a molar ratio of 1.52 in an amount of 0. 19 millimols of ferric chloride per mol of benzene so as to be 1.59 of chlorination degree (mol number of substituted chlorine atoms per mol of benzene ring), by which nuclear chlorination can be carried out in the para-selectivity of 86%. It is further described that the para-selectivity of 88% can be obtained when the chlorination is continued at 60° C. for 4.5 hours (a total of 10 hours) so as to be 1.96 of chlorination degree.

WO97/43041 discloses in Preparation Example 7 production of p-dichlorobenzene from benzene by reacting 1.84 mols of benzene with chlorine at 60° C. for 3.5 hours using a catalyst system consisting of 10-substituted 10H-phenothiazine/ferric chloride in a molar ratio of 1.2 in an amount of 0.22 millimols of ferric chloride per mol of benzene so as to be 1.72 of chlorination degree, by which nuclear chlorination can be carried out in a para-selectivity of 86%.

WO97/43041 discloses in Preparation Example 1 production of p-dichlorobenzene from benzene by reacting 2.18 mols of benzene with chlorine at 50° C. for 7 hours using a catalyst system consisting of 10-substituted 10H-phenothiazine/ferric chloride in a molar ratio of 5.1 in an amount of 1.33 millimols of ferric chloride per mol of benzene so as to be 1.48 of chlorination degree, by which nuclear chlorination can be carried out in a para-selectivity of 87%.

A matter common to EP126669, EP474074 and WO97/43041 (referred to as "prior 3 patents" hereafter) is molar ratio of 10-substituted-10H-phenothiazine/ferric chloride being 1 or more.

In the prior 3 patents, the reaction temperature in case of using benzene as a starting material is 60° C. except for Example 3 of EP474074 being 20° C.

In the prior 3 patents, the reaction temperature is 20° C. in case of Example 5 of EP126669 and Example 3 of EP474074, where the amount of ferric chloride is 1.52 millimols per mol of chlorobenzene (12.7 times of the amount in Example 3 of EP126669) and 2.46 millimols per mol of benzene (10.2 times of the amount in Example 1 of EP474074) and the ratio of substituted-10H-phenothiazine/ferric chloride is 1.6 and 1.0, respectively. The para-selectivity in Example 5 of EP126669 and that of Example 3 of EP474074 are 87.3% and 86.1% respectively, which are the best in each patent. These values are realized by reducing the reaction temperature and increasing an amount of the catalyst. The reason of it is believed that the reaction time does not remarkably increase even though the reaction temperature is low.

The reason why the reaction time is the same or up to only 11% increase, which means no remarkable increase in reaction time, in spite of reducing the reaction temperature, is believed to be based on the effect of increasing the amount of the catalyst.

In Example 6 of EP474074, the amount of ferric chloride is 0.42 millimols per mol of chlorobenzene (1.7 times of the amount in Example 1 of EP474074) and the ratio of substituted-10H-phenothiazine/ferric chloride is 1.0. The reaction is carried out at the reaction temperature of 70° C. for 2.5 hours, by which 60% by mol of chlorine is reacted to benzene. Although the reaction time becomes one a half by increasing the amount of the catalyst and elevating 10° C. the reaction temperature, the para-selectivity is only 82.0%.

In Preparation Example 7 of WO97/143041, it is described that nuclear chlorination in the para-selectivity of 86% can be carried out by chlorinating benzene at 60° C. for 3.5 hours using a catalyst system consisting of 10-substituted-10H-phenothiazine/ferric chloride in a molar ratio of 1.2 in an amount of 0.22 millimols per mol of benzene so as to be chlorination degree of 1.72. However, the reason why the reaction time becomes as short as 3.5 hours is not disclosed. Preparation Example 7 is distinctly different from Preparation Example 2 in a viewpoint that a part of the reaction mixture after reacting 7 hours in Preparation Example 12 has been used as a catalyst. Therefore, the reaction time becomes 10.5 hours in Example 7, because the process of Preparation Example 12 is added to the process of Preparation Example 7.

As be clear from the above-mentioned facts, these prior 3 patents neither disclose nor suggest the present invention, that is, "a process for preparing p-dichlorobenzene by carrying out nuclear chlorination of benzene and/or chlorobenzene (referred to as "starting material") for the reaction time of 1–4 hours by chlorine molecules, which comprises chlorinating using aluminum chloride and phenothiazine of the above formula (I) in such an amount that a molar ratio of [phenothiazine of the above formula (I)/aluminum chloride] is 0.1–0.9 and a ratio by millimol/mol of [aluminum chloride/starting material] is 0.1–3 so as to be a chlorination degree in a range of 1.2–2.5.

BEST MODES FOR CARRYING OUT THE INVENTION

Embodiments of the present invention will be illustrated in detail hereafter.

In the present invention, benzene and chlorobenzene as the starting materials are available on the market or can be prepared by methods described in technical literatures. It is, however, preferred to use benzene and chlorobenzene after distillation and, more preferably, those obtained by distillation after drying and/or in the presence of a drying agent. It is preferred to use them as early as possible and, preferably, immediately after distillation. Benzene and chlorobenzene may be used in a state of a mixture of them.

Aluminum chloride used in the present invention are available on the market. It may be prepared from metallic aluminum. The amount of aluminum chloride used is 0.1–3 millimols, preferably, 0.2–1.5 millimols, and more preferably 0.3–1 millimols per mol of benzene and/or chlorobenzene as the starting material.

Phenothiazines represented by the above formula (I) used in the present invention are available on the market. Alternatively, they can be prepared by methods described in technical literatures. Phenothiazines of the formula (I) wherein the group A is $CF_3(CF_2)_nCO-$ (n=0, 1 or 2) can be prepared by, for example, a method described in Japanese Patent Application Laid-open HEI 9-301939 or by similar methods. Phenothiazines of the formula (I) wherein the group A is a substituted or unsubstituted phenoxycarbonyl of the formula (II) can be prepared by, for example, a method described in WO97/43041 or a method according to it.

Examples of phenothiazines represented by the formula include, as preferable phenothiazines, 10-chlorocarbonyl-10H-phenothiazine, 10-dichloroacetyl-10H-phenothiazine, 2-chloro-10-chlorocarbonyl-10H-phenothiazine, 10-trifluoroacetyl-10H-phenothiazine, 10-pentafuluoropropionyl-10H-phenothiazine, 10-heptafluorobutyroyl-10H-phenothiazine, 10H-phenothiazine-10-carboxylic acid phenyl ester, 10H-phenothiazine-10-carboxylic acid 4-chlorophenyl ester, 10H-phenothiazine-10-carboxylic acid 4-methylphenyl ester, 10H-phenothiazine-10-carboxylic acid 4-methoxyphenyl ester, 2-chloro-10H-phenothiazine-10-carboxylic acid phenyl ester, and nuclear chlorinated 10H-phenothiazine-10-carboxylic acid phenyl ester.

The amount of the phenothiazine represented by the above formula (I) is in a range of 0.1–0.9 mols, preferably 0.2–0.8 mols and more preferably 0.3–0.7 mols.

In the present invention, nuclear chlorination is carried out using a necessary or excess amount of gaseous or liquid chlorine so as to be a desired chlorination degree. The chlorination degree is 1.2–2.5, preferably 1.3–2.2 and more preferably 1.4–2.

The nuclear chlorination reaction in the present invention may be carried out, if desired, in a reaction solvent. As the reaction solvent, halogenated hydrocarbons such as dichlorobenzene, 1,2-dichloroethane, 1,2-dichloropropane, dichloromethane, chloroform, carbon tetrachloride, etc. can be used.

The reaction temperature in the present invention is preferably in a range of 30–80° C., more preferably 40–70° C. and particularly 45–55° C.

The reaction time in the present invention is in a range of 1–4 hours, preferably 1–3.5 hours and particularly 1.5–3.2 hours.

The nuclear chlorination is performed under such a condition that the para-selectivity of the resulted reaction mixture becomes preferably 83% or more, more preferably 85% or more, and particularly 86% or more, by combining the above-mentioned reaction conditions.

The process for preparing p-dichlorobenzene according to the present invention is characterized, as mentioned above, by carrying out the reaction using a catalyst system consisting of aluminum chloride and phenothiazine represented by the formula (I). However, it is possible to use a method comprising taking out a product from the reaction mixture after nuclear chlorination of benzene and/or chlorobenzene as the starting material by distillation, and repeatedly carrying out nuclear chlorination by adding benzene and/or chlorobenzene to the residue as the catalyst system, or a method comprising carrying out nuclear chlorination by adding a part of the reaction mixture as the catalyst system to benzene and/or chlorobenzene. In these process of the present invention, the aluminum chloride and/or phenothiazine represented by the formula (I) may be added on the way of the reaction step.

EXAMPLES

Example 1

(Chlorination of Benzene Using a Catalyst System Consisting of 10H-phenothiazine-10-carboxylic Acid Phenyl Ester and Aluminum Chloride in a Molar Ratio of 0.60)

To 150 g (1.92 mols) of benzene in a light-shielding reactor were added aluminum chloride 0.09 g (0.675 mmols; 0.35 mmols per mol of benzene) and 10H-phenothiazine-10-carboxylic acid phenyl ester 0.13 g (0.41 mmols; molar ratio of phenothiazine/aluminum chloride is 0.60) at 50° C. with stirring. Chlorination was carried out by reacting at the same temperature for 150 minutes with blowing a chlorine gas so as to be a chlorination degree of 1.62 on the basis of benzene.

It was confirmed by gas chromatography analysis that the reaction mixture had the following composition. Benzene 0.02%, chlorobenzene 31.67%, o-cichlorobenzene 9.13%, m-dichlorobenzene 0.11%, p-dichlorobenzene 58.98% and trichlorobenzene 0.09%.

The para-selectivity calculated based on the above mentioned composition was 86.60%.

Example 2

(Chlorination of Benzene Using a Catalyst System Consisting of 10-chlorocarbonyl-10H-phenothiazine and Aluminum Chloride in a Molar Ratio of 0.50)

To 150 g (1.92 mols) of benzene in a light-shielding reactor were added aluminum chloride 0.09 g (0.67 mmols; 0.35 mmols per mol of benzene) and 10-chlorocarbonyl-10H-phenothiazine 0.09 g (0.34 mmols; molar ratio of phenothiazine/aluminum chloride is 0.50) at 50° C. with stirring. Chlorination was carried out by reacting at the same temperature for 170 minutes with blowing a chlorine gas so as to be a chlorination degree of 1.62 on the basis of benzene.

It was confirmed by gas chromatography analysis that the reaction mixture had the following composition. Benzene 0.03%, chlorobenzene 32.15%, o-cichlorobenzene 9.87%, m-dichlorobenzene 0.15%, p-dichlorobenzene 57.67% and trichlorobenzene 0.13%.

The para-selectivity calculated based on the above mentioned composition was 85.38%.

Capability of Exploitation in Industry

According to the present invention, p-dichloro-benzene can be obtained in a para-selectivity equal to or higher than that of the prior methods by carrying out nuclear chlorination of benzene and/or the chlorobenzene using aluminum chloride and phenothiazine represented by the above formula (I) in the above-mentioned amounts. Furthermore, the chlorination can be carried out in a shorter reaction time than the prior methods.

The invention claimed is:

1. A process for preparing p-dichlorobenzene by nuclear chlorination of benzene and/or chlorobenzene as starting material with chlorine molecules, which comprises chlorinating the starting material using aluminum chloride in an amount of 0.1–3 millimols per mol of said starting material and phenothiazine represented by the following formula(I) in an amount of 0.1–0.9 mols per mol of aluminum chloride so that a chlorination degree is in a range of 1.2–2.5:

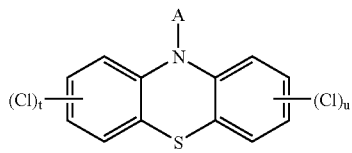
(I)

wherein t is an integer of 0–4; u is an integer of 0–4; A is a halocarbonyl group; a group represented by $CH_xX^1_yCO-$, wherein $X^1$ is a chlorine atom or a bromine atom, x is an integer of 0–2, and y is an integer of 1–3; a group represented by $CF_3(CF_2)_nCO-$, where n is an integer of 0–2; or a group represented by the following formula(II):

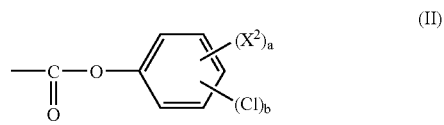
(II)

wherein $X^2$ is a halogen atom, an alkyl group having 1–4 carbon atoms, an alkoxy group having 1–4 carbon atoms, a nitro group or a cyano group; a is an integer of 0–5; a plurality of $X^2$ is identical or different respectively when a is 2 or more; and b is an integer of 0–5, but (a+b) is an integer of 5 or less.

* * * * *